(12) United States Patent
Wang et al.

(10) Patent No.: US 7,999,105 B2
(45) Date of Patent: Aug. 16, 2011

(54) PROCESS FOR THE PREPARATION OF 3-HYDROXYMORPHINAN DERIVATIVES

(75) Inventors: Peter X. Wang, Clarkson Valley, MO (US); Tao Jiang, St. Louis, MO (US); Gary L. Cantrell, Troy, IL (US); David W. Berberich, St. Peters, MO (US); Frank W. Moser, Arnold, MO (US); Jian Bao, Chesterfield, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 425 days.

(21) Appl. No.: 12/372,788

(22) Filed: Feb. 18, 2009

(65) Prior Publication Data

US 2009/0221825 A1   Sep. 3, 2009

Related U.S. Application Data

(60) Provisional application No. 61/032,435, filed on Feb. 29, 2008.

(51) Int. Cl.
*C07D 489/02* (2006.01)
*C07D 221/22* (2006.01)
*C07F 5/02* (2006.01)
(52) U.S. Cl. .................. 546/45; 546/13; 546/74
(58) Field of Classification Search .............. 546/45, 546/13, 74
See application file for complete search history.

(56) References Cited

U.S. PATENT DOCUMENTS

| | | | |
|---|---|---|---|
| 4,451,470 | A | 5/1984 | Ganti |
| 5,869,669 | A | 2/1999 | Huang et al. |
| 6,008,355 | A | 12/1999 | Huuang et al. |
| 6,172,078 | B1 | 1/2001 | Nagase et al. |
| 6,177,567 | B1 | 1/2001 | Chiu et al. |
| 6,469,170 | B1 | 10/2002 | Chiu et al. |
| 6,864,370 | B1 | 3/2005 | Lin et al. |
| 7,153,966 | B2 | 12/2006 | Casner et al. |

OTHER PUBLICATIONS

Manmade et al., "Total Synthesis of Racemic 3 Deoxy-7 8 Di Hydro Morphinone", Journal of Organic chemistry, vol. 47, No. 9, 1982, pp. 1717-1721, XP 002530161.
Trauner et al., "New ventures in the construction of complex heterocycles: Synthesis of morphine and hasubanan alkaloids", Synthesis 199804 DE, Apr. 1998, pp. 654-664, XP 002530162.
Gates, "The Synthesis of Racemic β-Δ⁶-Dihydrodesoxycodeine Methyl Ether", Chemistry and Industry, Communications to the Editior, Oct. 1950, vol. 72, pp. 4839-4840.
Gates et al., "The Synthesis of Morphine", Chemistry and Industry, 1956, vol. 78, pp. 1380-1393.
Gates et al., "The Closure of the Oxide Bridge in the Morphine Series", Chemistry and Industry, Dec. 22, 1956, pp. 1506-1507.
Gates et al., "The Closure of the Oxide Bridge in the Morphine Series", Chemistry and Industry, Nov. 5, 1962, vol. 84, pp. 4125-4130.
Goodwin, "Leucoxine and Leucoxylonine", Chemistry and Industry, Jun. 11, 1960, pp. 691-692.
Goto et al., "On the Acetolysis of (+)-1,5,7-Tribromodihydrothebainone and (+)-1,7-Dibromodihydrocodeinone", Proc. Japan Acad., 1960, vol. 36:3, pp. 145-150.
Hutchinson et al., "Synthesis and Opioid Binding Properties of 2-Chloroacrylamido Derivatives of 7,8-Dihydromorphinans", Bioorganic & Medicinal Chemistry Letters, 1996, vol. 6, No. 13, pp. 1563-1566.
Kotick et al., "Analgesic Narcotic Antagonists. 8. 7α-Alkyl-45α-epoxymorphinan-6-ones", J. Med. Chem., 1981, 24, pp. 1445-1450.
Manmade et al., "Total Synthesis of (±)-3-Deoxy-7,8-dihydromorphinone", J. Org. Chem., 1982, 47, pp. 1717-1721.
Bhargava, "Synthesis of 2'-Amino-17-cyclopropylmethyl-6,7-dehydro-3,14-dihydroxy-4,5α-epoxy-67:4',5'-thiazolmorphinan from Naltrexone [1]", J. Heterocyclic Chem., 1997, vol. 34, pp. 1195-1203.
Olieman et al., "Recueil des Travaux Chimiques des Pays-Bas Journal of the Royal Netherlands Chemical Society", 1978, vol. 87:2, pp. 31-35.
Small et al., "The Addition of Organomagnesium Halides to Pseudocodeine types. IV. Nuclear-Substituted Morphine Derivatives", J. Org. Chem., 1938, vol. 3, pp. 204-232.
Weller et al., "A Practical Synthesis of codeine from Dihydrothebainone", Journal of Medicinal Chemistry, vol. 19, No. 10, 1976, pp. 1171-1175.
Gao et al., "Boron Tribromide-Catalyzed Rearrangement of 7,7-Diphenylhydromorphone to 6,7-Diphenylmorphine: A Novel Conversion of Ketones to Allylic Alcohols", Journal of Organic Chemistry, 1996, 61(7), pp. 2466-2469.
Lattanzi et al., "Synthesis and Biological Evaluation of 14-Alkoxymorphinans.22.Influence of the 14-Alkoxy Group and the Substitution in Position 5 in 14-Alkoxymorphinan-6-ones on in Vitro and in Vivo Activities", J. Med. Chem., 2005, 48(9), pp. 3372-3378.
Spetea et al., "Synthesis and Biological Evaluation of 14-Alkoxymorphinans. 21. Novel 4-Alkoxy and 14-Phenylpropoxy Derivatives of the □ Opiod Receptor Antagonist Cyprodime", J. Med. Chem., 2004, 47(12), pp. 3242-3247.
Schtz et al., "Synthesis and Biological Evaluation of 14-Alkoxymorphinans. 20. 14-Phenylpropoxymethopon: An Extremely Powerful Analgesic", J. Med. Chem., 2003, 46(19), pp. 4182-4187.
Greiner et al., "Synthesis and Biological Evaluation of 14-Alkoxymorphinans. 18. N-Substituted 14-Phenylpropyloxymorphinan-6-ones with Unanticipated Agonist Properties: Extending the Scope of Common Structure-Activity Relationships", J. Med. Chem., 2003, 46(9), pp. 1758-1763.
Tanaka et al., "Solid-Phase Synthesis of Naltrindole Derivatives Using Fischer Indole Synthesis Based on One-Pot Release and Cyclization Methodology", Org. Lett., 2003, 5(8), pp. 1159-1162.
Cain et al., "Sequential Benzylic Oxidation of Naloxone 3-Methyl Ether", Synthetic Communications, 2003, 30(24), pp. 4513-4521.
Krassnig et al., A New and Efficient Synthesis of the μ Opioid Receptor Antagonists 14-O-Methyl- and 14-O-Ethylnaloxone and -Naltrexone, Heterocycles, 1998, vol. 47, No. 2, pp. 1029-1032.

(Continued)

*Primary Examiner* — Charanjit Aulakh

(57) ABSTRACT

Processes are described for the synthesis of 3-hydroxymorphinan derivatives by hydrolysis of side products from the O-demethylation of 3-methoxymorphinan derivatives.

20 Claims, No Drawings

OTHER PUBLICATIONS

Andre et al., "O-Demethylation of Opioid Derivatives with Methane Sulfonic Acid / Methionine: Application to the Synthesis of Nalxone and Analogues", Synthetic Communications, 1992, 22(16), pp. 2313-2327.

Schmidhammer et al., "161.Synthesis and biological Evaluation of 14-Alkoxymorphinans part 8) 14-Methoxymetopon, an Extremely Potent Opioid Agonist", Helvetica Chimica Acta, 1990, vol. 73, pp. 1784-1787.

Schmidhammer, "134.Synthesis and Biological Evaluation of 14-Alkoxymiorphinans Part 41) Opioid Agonists and Partial Opioid Agonists in a Series of N-(Cyclobutylmethyl)-14-methoxymorphinan-6-ones", Helvetica Chimica Acta, 1989, vol. 72, pp. 1233-1240.

Schmidhammer, "191.Synthesis Structure Elucidation, and Pharmacological Evaluation of 5-Methyl-oxymorphone (=4,5x-Epoxy-3,14-dihydroxy-5,17-dimethylmorphinan-6-one)", Helvetica Chimica Acta, 1988, vol. 72, pp. 1801-1804.

Bakker et al., "The chemistry of small ring compounds. Part 36 CIDNP effects during the oxidation of substituted cyclopropanone methyl hemiacetals by di-*tert*-butyl diperoxyoxalate", Rec. Trav. Chim., Feb. 1977, 96, pp. 31-35.

PROCESS FOR THE PREPARATION OF 3-HYDROXYMORPHINAN DERIVATIVES

FIELD OF THE INVENTION

The present invention generally relates to processes for the synthesis of intermediate or end product morphinans. More specifically, the invention is directed to improved processes for the synthesis of 3-hydroxymorphinan derivatives by O-demethylation of 3-methoxymorphinan derivatives.

BACKGROUND OF THE INVENTION

Oxymorphone is usually made by O-demethylation of oxycodone with a variety of O-demethylation reagents such as $BBr_3$, $MeSO_3H$/methionine and HBr. The yield for this O-demethylation reaction ranges from 30% to 80% depending on the particular process conditions used. A low yield may result as a consequence of the strong acids or Lewis acids reacting with the functional groups of, for example, oxycodone and the product oxymorphone. Thus, use of these reagents leads to unavoidable reductions in the yield of oxymorphone due to formation of side products.

SUMMARY OF THE INVENTION

Among the various aspects of the present invention is the provision of a process for the conversion of the side products from the O-demethylation of 3-methoxymorphinan derivatives to 3-hydroxymorphinan derivatives.

Another aspect is a process for the preparation of a morphinan compound corresponding to the formula:

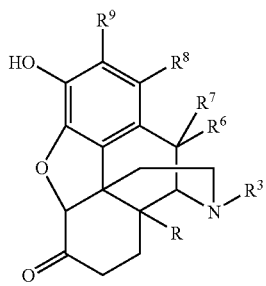

(III)

the process comprising hydrolyzing a compound corresponding to the formula (I):

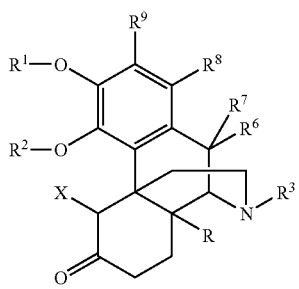

(I)

in a protic solvent to form an intermediate compound (II) corresponding to the formula

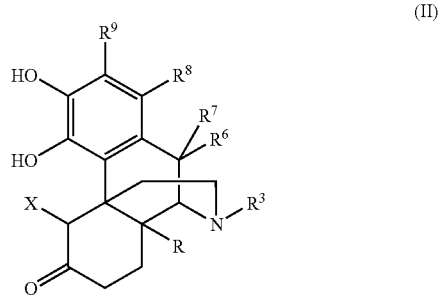

(II)

and, heating a mixture comprising an aqueous solvent and the compound (II), in an aqueous solvent, at a pH of about 1 to about 6 to form compound (III), wherein:

R is selected from the group consisting of hydrogen, alkyl, aryl, acyl, —$SR^4$, —$OR^4$, and —$NR^4R^5$;

$R^1$ and $R^2$ are independently selected from the group consisting of hydrogen, alkyl, $B(OH)_2$, and $R^1$ and $R^2$, along with the atoms to which they are attached, form a 5-membered ring having a fifth ring member $B(OH)$; provided, however, that at least one of $R^1$ and $R^2$ is $B(OH)_2$ or that $R^1$ and $R^2$ form the 5-membered ring;

$R^3$ is selected from the group consisting of hydrocarbyl, substituted hydrocarbyl, and a nitrogen protecting group;

$R^4$ and $R^5$ are independently selected from the group consisting of hydrogen, alkyl, aryl, and acyl;

$R^6$ and $R^7$ are independently selected from the group consisting of hydrogen, halogen, hydroxyl, $NH_2$, SH, hydrocarbyl, and substituted hydrocarbyl, wherein $R^6$ and $R^7$ may together form a group selected from the group consisting of =O and =S;

$R^8$ and $R^9$ are independently selected from the group consisting of hydrogen, halogen, hydroxyl, $NH_2$, CN, hydrocarbyl, and substituted hydrocarbyl; and X is selected from the group consisting of chloro, bromo, and iodo.

Yet another aspect is a process for the preparation of a morphinan compound (III) corresponding to the formula:

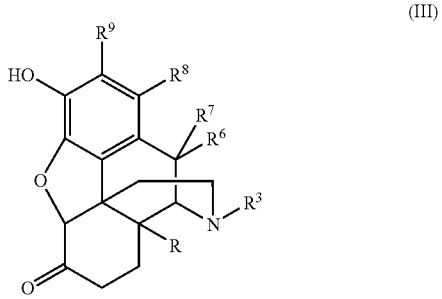

(III)

the process comprising heating a mixture comprising an aqueous solvent and a compound (II), corresponding to the formula:

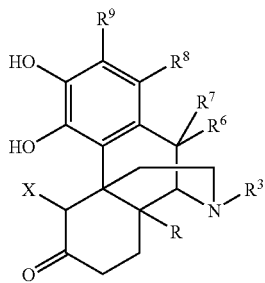

(II)

in an aqueous solvent, at a pH of about 1 to about 6 to form compound (III) wherein R, $R^3$, $R^4$, $R^5$, $R^6$, $R^7$, $R^8$, $R^9$, and X are as defined above.

A further aspect of the invention is a morphinan compound, or pharmaceutically acceptable salt thereof, the compound corresponding to the formula:

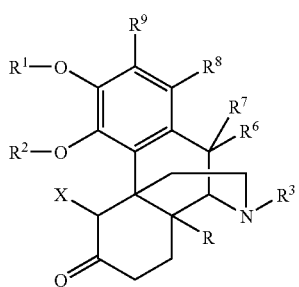

(I)

wherein R, $R^1$, $R^2$, $R^3$, $R^4$, $R^5$, $R^6$, $R^7$, $R^8$, $R^9$, and X are as defined above.

Another aspect is a morphinan compound, or a pharmaceutically acceptable salt thereof, the compound corresponding to the formula:

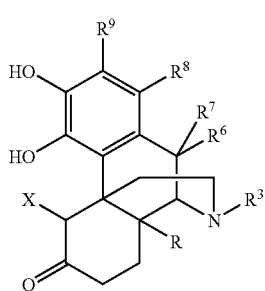

(II)

wherein R, $R^3$, $R^4$, $R^5$, $R^6$, $R^7$, $R^8$, $R^9$, and X are as defined above.

Other objects and features will be in part apparent and in part pointed out hereinafter.

DETAILED DESCRIPTION

Generally, various aspects of the process described herein include the hydrolysis of a major side product in the preparation of 3-hydroxymorphinan derivatives (III) by O-demethylation of 3-methoxymorphinan derivatives.

Scheme A

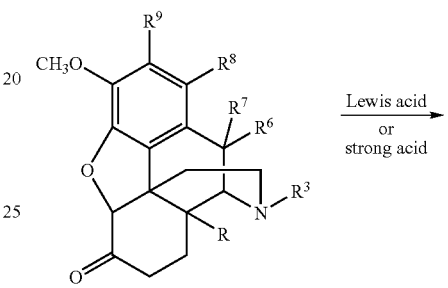

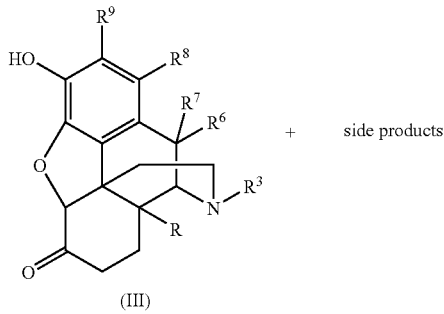

(III)

As seen from Scheme A, a methyl group attached to the oxygen at the C3 position of a morphinan compound is removed to form an O-demethylated morphinan compound. This demethylation reaction occurs under reaction conditions that produce various side products. When using boron-based Lewis acids, some of the side products of this demethylation reaction are compounds of formula I.

As depicted in Scheme 1, these side products have been identified as various isomers of compound I that include boron complexes as described below. These compound I isomers are hydrolyzed in a protic solvent to form isomers of compound II. The hydrolysis reaction decreases the pH of the reaction mixture. The method comprises increasing the pH of the reaction mixture to about 1 to about 6 such that compound II is hydrolyzed in the presence of heat to form compound III.

Scheme 1

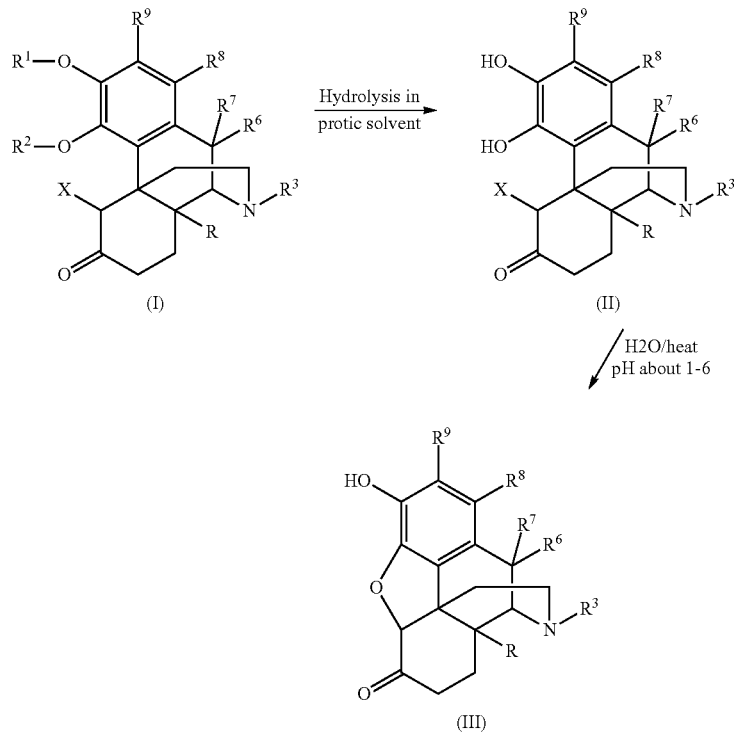

The identity of R, $R^1$, $R^2$, $R^3$, $R^4$, $R^5$, $R^6$, $R^7$, $R^8$, $R^9$, and X are identified above.

In some of the process embodiments, the reaction of a 3-methoxymorphinan compound with $BBr_3$ forms boric derivatives that are hydrolyzed to a 3-hydroxymorphinan compound in an aqueous solution. Significant side products are boric derivatives of 5-bromo-3,4-oxymorphinan isomers (e.g., compound IA); the percent yield of these side products is about 15% to 35%. The boric derivatives may be converted to 5-bromo-3,4-dihydroxymorphinan isomers of compound IIA by a hydrolysis reaction in a protic solvent as shown in Scheme 1A below. The reaction mixture comprising the isomers of compound IIA becomes very acidic (pH less than 0) after boric complexes of compound IA are hydrolyzed. Heating the reaction mixture resulted in the decomposition of the 3-hydroxymorphinan derivatives and isomers of compound IIA. Alternatively, if the pH of the reaction mixture was increased to a pH greater than 5, the 3-hydroxymorphinan did not decompose, but isomers of compound IIA did begin to decompose. Greater than 50% of the amount of the side products (e.g., compound IIA) decomposed when treated with a base at a pH of about 7 to 10. On treatment of compound IIA with a strong base like 1 N NaOH, one isomer was partially converted to 3-hydroxymorphinan but the other isomer decomposed. Thus, control of the pH during the conversion of isomers of compound IIA to compound III is important.

Scheme 1A

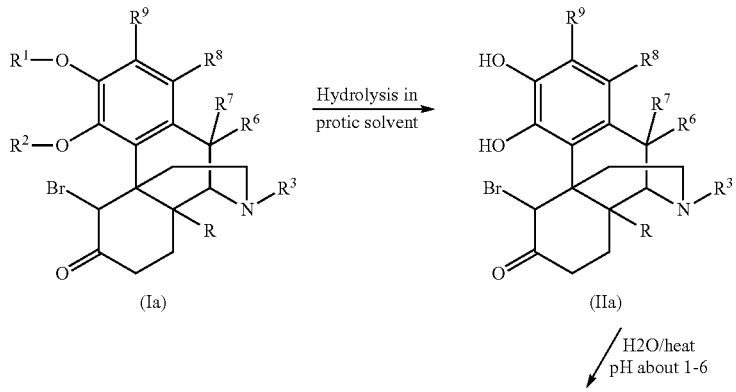

-continued

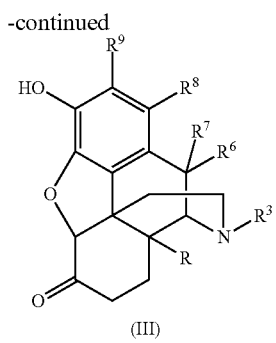

(III)

The present invention further includes processes for conversion of isomers of compound II into 3-hydroxymorphinan derivatives (e.g., compound III). These processes allow the transformation of isomers of compound II to 3-hydroxymorphinan derivatives at a pH of about 1 to about 6 with a minimum amount of decomposition from reaction of an α-Br-ketone with water or hydroxide.

Solid 3-hydroxymorphinan compound is recovered in high yield after the processes of the invention are carried out and the pH is adjusted to greater than about 8. The addition of the processes described herein to various processes to prepare 3-hydroxymorphinan derivatives provides solvent savings and time savings in unit operations and overall processing as compared to conventional processes for preparing 3-hydroxymorphinan derivatives, such as oxymorphone.

3-Methoxymorphinan derivatives, such as oxycodone, used in the O-demethylation reaction can be prepared by various methods known in the art. For example, various methods for preparing oxycodone are described in U.S. Pat. Nos. 7,153,966; 6,864,370; 6,469,170; 6,177,567; and 6,008,355; incorporated by reference herein in their entirety.

For purposes of discussion, the ring atoms of the morphinans of the present invention are numbered as follows.

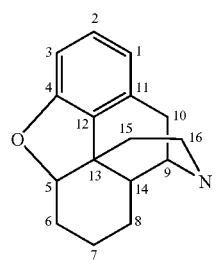

Schemes 1 and 1A above depict the chemical conversion of compound I to compound II and further to the desired product compound III; oxymorphone is a compound of Formula III. Each of these compounds is described in more detail below.

Compound III

The desired product is a compound having formula III. These compounds can be prepared from the side products (e.g., compound I) by the processes described herein. Thus, the processes of the present invention are employed to prepare compounds having formula III:

(III)

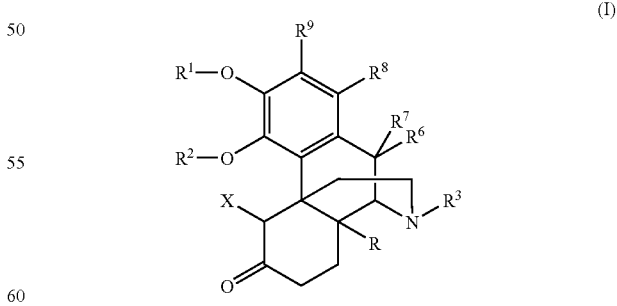

wherein R, $R^3$, $R^4$, $R^5$, $R^6$, $R^7$, $R^8$, and $R^9$ are as defined above. In some embodiments, $R^3$ is alkyl, allyl, aryl, or acyl. In various preferred embodiments, $R^3$ is alkyl. In some of these embodiments, $R^3$ is methyl, cyclopropyl, isobutyl, or cyclobutyl; preferably, $R^3$ is methyl. In certain embodiments, R is hydrogen or hydroxyl; preferably, R is hydroxyl. In some of these embodiments, $R^3$ is methyl and R is hydrogen or hydroxyl; in preferred embodiments, $R^3$ is methyl and R is hydroxyl.

The optical activity of compounds having formula III may be (−) or (+). Furthermore, the configuration of the chiral carbons, C5, C13, C14, and C9, respectively, may be RRRR, RRSR, RRRS, RRSS, RSRR, RSSR, RSRS, RSSS, SRRR, SRSR, SRRS, SRSS, SSRR, SSSR, SSRS, or SSSS.

Compound I

The side products from the O-demethylation of 3-methoxymorphinan derivatives has been identified as compounds having formula I:

(I)

wherein R, $R^1$, $R^2$, $R^3$, $R^4$, $R^5$, $R^6$, $R^7$, $R^8$, $R^9$, and X are defined as above. Compounds of formula I may be converted to compounds of formula II using the processes described herein.

In some embodiments, $R^3$ is alkyl, allyl, aryl, or acyl. In various preferred embodiments, $R^3$ is alkyl. In some of these embodiments, $R^3$ is methyl, cyclopropyl, isobutyl, or cyclobutyl; preferably, $R^3$ is methyl. In certain embodiments, R is hydrogen or hydroxyl; preferably, R is hydroxyl. Also, X may be bromo or chloro; preferably, X is bromo.

In various embodiments, at least one of $R^1$ or $R^2$ is $B(OH)_2$ and the other of $R^1$ or $R^2$ is hydrogen; or $R^1$ and $R^2$ form a 5-membered ring having a fifth ring member B(OH). In some of these embodiments, $R^1$ or $R^2$ is $B(OH)_2$ and the other of $R^1$ or $R^2$ is hydrogen; preferably, $R^1$ is hydrogen and $R^2$ is $B(OH)_2$. In other embodiments, $R^1$ and $R^2$ form a 5-membered ring having a fifth ring member B(OH).

In various embodiments, $R^3$ is methyl, cyclopropyl, isobutyl, or cyclobutyl, R is hydrogen or hydroxyl, X is bromo, and one of $R^1$ or $R^2$ is $B(OH)_2$ and the other of $R^1$ or $R^2$ is hydrogen; or $R^1$ and $R^2$ form a 5-membered ring having a fifth ring member B(OH); in preferred embodiments, $R^3$ is methyl, R is hydroxyl, X is bromo, $R^1$ is hydrogen, and $R^2$ is $B(OH)_2$.

The optical activity of compounds having formula I may be (−) or (+). Furthermore, the configuration of the chiral carbons, C13, C14, and C9, respectively, may be RRR, RRS, RSR, RSS, SRR, SRS, SSR, or SSS.

Compound II

An intermediate in the process of the present invention is a compound having formula II:

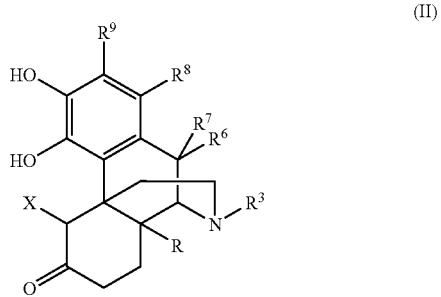

(II)

wherein R, $R^3$, $R^4$, $R^5$, $R^6$, $R^7$, $R^8$, $R^9$, and X are as defined above. This compound is prepared by hydrolyzing compounds of formula I in a protic solvent.

In some embodiments, $R^3$ is alkyl, allyl, aryl, or acyl. In various preferred embodiments, $R^3$ is alkyl. In some of these embodiments, $R^3$ is methyl, cyclopropyl, isobutyl, or cyclobutyl; preferably, $R^3$ is methyl. In certain embodiments, R is hydrogen or hydroxyl; preferably, R is hydroxyl. In certain embodiments, X is bromo or chloro; preferably, X is bromo. In some of these embodiments, $R^3$ is methyl, R is hydrogen or hydroxyl, and X is bromo; in preferred embodiments, $R^3$ is methyl, R is hydroxyl, and X is bromo.

The optical activity of compounds having formula II may be (−) or (+). Furthermore, the configuration of C13, C14, and C9, respectively, may be RRR, RRS, RSR, RSS, SRR, SRS, SSR, or SSS.

Process Conditions

Conversion of Compound I to Compound II

Generally, the hydrolysis reaction converting compounds of formula I to compounds of formula II takes place in a protic solvent. The protic solvent may be selected from the group consisting of water, methanol (MeOH), ethanol (EtOH), isopropyl alcohol (IPA), and combinations thereof. In various preferred embodiments, the solvent is water.

Conversion of Compound II to Compound III

Typically, the hydrolysis reaction to convert compounds of formula II to compounds of formula III occurs at a pH of about 1 to a pH of about 6. In order for this reaction to occur at this pH, a base is added after compounds of formula I are converted to compounds of formula II. In various embodiments, the pH of this hydrolysis reaction is about 2 to about 4; preferably, about 3 to about 4.

Further, this hydrolysis reaction mixture is heated to a temperature of about 20° C. to about 120° C. during the process of conversion to compounds of formula II. In some embodiments, the reaction mixture is heated to a temperature of about 60° C. to about 90° C.

Definitions

The compounds described herein may have asymmetric centers. Compounds of the present invention containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R_2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, n-butyl, isobutyl, tert-butyl, pentyl, hexyl, cyclopropyl, cyclobutyl, cyclopentyl, cyclohexyl, and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "allyl" refers to an alkene hydrocarbyl group comprising a vinyl group attached to a methylene group.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following non-limiting examples are provided to further illustrate the present invention.

Example 1

Reaction of Oxycodone with $BBr_3$, Followed By Hydrolysis

Oxycodone (20.0 g) was suspended in chlorobenzene (300 mL) in a reactor 1. Boron tribromide ($BBr_3$, 20.0 mL) was added slowly to form a suspension (an exothermic reaction was observed). The reaction temperature was maintained below 25° C. during the addition. Stirring at 15 to 25° C. was carried out for 14 hours. The solution was added to a reactor 2 that had been pre-filled with 170 mL of water. The temperature reached 50 to 55° C. and was maintained at a temperature below 65° C. during the addition. After the transfer, some solid residue still remained in reactor 1.

The mixture in reactor 2 was stirred at 60 to 65° C. to dissolve the solids for about 10 minutes and then allowed to separate into two clear layers. The aqueous solution in reactor 2 was transferred back to reactor 1. After stirring at 60 to 65° C. for 15 to 30 minutes, all the solids were in solution in reactor 1. The organic layer in reactor 2 was extracted with $H_3PO_4/H_2O$ solution (5% wt/wt, 20 mL) and the aqueous layer was transferred to reactor 1. The solution in reactor 1 was maintained at 60 to 65° C., extracted with chlorobenzene (40 mL), and then separated into two phases. The organic layer in reactor 1 was transferred to reactor 2 to give 350 mL of solution (combined organic layer) that was discarded. To the aqueous layer in reactor 1 at 60 to 65° C., 50% NaOH was added. The pH was adjusted with 50% NaOH (about 30 mL) to pH 2.5 to give a small amount of precipitate. The temperature was maintained below 80° C. during the addition of NaOH. After heating at 80° C. for 2.5 hours, a solution formed.

The hot solution in reactor 1 was cooled to room temperature. Concentrated ammonium hydroxide (about 40 mL) was added and the pH was adjusted to 9.5. Stirring was continued at room temperature for 10 minutes at pH 9.5. Pure oxymorphone (0.2 g) was added to act as a seed for crystallization. Stirring was continued at room temperature for 2 hours. The solid was separated by filtration and washed with water (2×50 mL). The wet solid was dried under vacuum (40 to 60 mmHg) at 75° C. for 16 hours to give 17.57 g of solid oxymorphone. Yield: crude wt./wt. %, weight of crude product/weight of starting material was 88%; mol/mol %, oxymorphone in the product/oxycodone in the starting material was 77%.

Example 2

Conversion of By-products to Oxymorphone Under Acidic Conditions

Oxycodone (10.0 g) was suspended in chloroform ($CHCl_3$, 150 mL) in a reactor A. Boron tribromide ($BBr_3$, 10.0 mL)

was added slowly and an exotherm was observed. The reaction temperature was maintained below 25° C. during the addition. Stirring of the mixture was continued at room temperature for 14 hours. The material was transferred to reactor B that was pre-filled with 85 mL of water. The temperature reached 50 to 55° C. and was maintained below 55° C. during the addition. After transfer of the mixture to reactor B, some solid residue still remained in reactor A. The mixture in reactor B was stirred at 50 to 55° C. to dissolve the solid (about 15 minutes) and then when stirring was stopped, the mixture separated into two clear layers. The aqueous solution in reactor B was transferred back to reactor A. The mixture was stirred at 50 to 55° C. for 15 to 30 minutes to dissolve all the solids. The organic layer in reactor B was extracted with $H_3PO_4/H_2O$ solution (2% wt/wt, 15 mL). The aqueous extraction was transferred to reactor A. The solution in reactor A was extracted with dichloroethane (30 mL) and then allowed to separate into two phases.

The aqueous layer was then separated into two portions, where 10 mL of the aqueous layer was added to flask A and another 10 mL of the aqueous layer was added to flask B. The solution in flask A was heated 80° C. for 2 hours and cooled to room temperature. The solution in flask A was then diluted to 100 mL with 1% acetic acid in water for HPLC analysis (sample 2-A). The solution in flask B was treated with 50% NaOH to pH 2.6 and was then heated 80° C. for 2 hours and cooled to room temperature. The solution in flask B was then diluted to 100 mL with 1% acetic acid in water for HPLC analysis (sample 2-B). The data in Table 1 are the area of oxymorphone, area/area % of oxymorphone, and area/area % of 5-Bromo-14-hydroxymorphinane isomers (IIB), as analyzed by HPLC.

TABLE 1

Yield of Compounds

| Samples | pH | Area of oxymorphone | Area % of oxymorphone | Area % of IIB |
|---|---|---|---|---|
| 2-A | less than 0 | 1198598 | 76.9% | 16% |
| 2-B | 2.6 | 1420087 | 90.11% | 1.9% |

The isomers IIA on sample 2-B were almost completely hydrolyzed to oxymorphone at pH 2.6 at 80° C. for 2 hours.

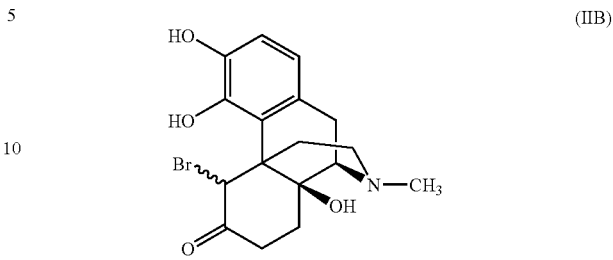
(IIB)

Example 3 pH Study for Conversion to Oxymorphone

The process of Example 2 through the extraction with dichloroethane was used to produce a mixture containing oxymorphone and isomers of compound IIB. This mixture was added to five vials (3.0 mL for each vial). Sample 3.1 was set aside at room temperature for 2 hours and diluted to 10.0 mL for HPLC analysis. Samples 3.2 to 3.6 were diluted to 6.0 mL with the reagents as shown in Table 2 to a predetermined pH value. Samples 3.1 to 3.6 were heated at 95° C. for 2 hours. The solution in each vial was then diluted to 10.0 mL for HPLC analysis. Table 3 shows the results of the HPLC analysis.

TABLE 2

Yield of Oxymorphone

| Entries | Reagents | pH | Oxymorphone peak area |
|---|---|---|---|
| 3.1 | 0 | <0 | 4755385 |
| 3.2 | $NaH_2PO_4/H_2O$ | 0.7 | 5550293 |
| 3.3 | $NaH_2PO_4/H_2O$ | 1.3 | 6476004 |
| 3.4 | $NaH_2PO_4/H_2O$ | 2.6 | 6688881 |
| 3.5 | $NaH_2PO_4$/NaOH | 5.2 | 5496622 |
| 3.6 | $NaH_2PO_4$/NaOH | 9.0 | 5058953 |

TABLE 3

HPLC Analysis

| Entries | Oxymorphone (mg/mL) | Oxymorphone Peak Area | Oxymorphone % Area | IIB Isomers % Area | Decomposed Materials % Area |
|---|---|---|---|---|---|
| 3.1 | 1.9765 | 4755385 | 58.30 | 30.55 | |
| 3.2 | 2.3069 | 5550293 | 71.18 | 13.17 | |
| 3.3 | 2.6916 | 6476004 | 82.47 | 8.33 | |
| 3.4 | 2.7801 | 6688881 | 88.14 | | 3.15 |
| 3.5 | 2.2846 | 5496622 | 67.98 | | 5.1 |
| 3.6 | 2.1027 | 5058953 | 63.71 | | 22.49 |

Entries 3.2 to 3.6 in Table 3 showed that the 5-bromo-14-hydroxymorphinane isomers of compound IIB were converted to oxymorphone in a pH range from about 0.7 to about 9.0. At a pH of about 9, a significant portion of the IIB isomers decomposed. Further, the maximum yield of oxymorphone was obtained at a pH of about 2.6.

What is claimed is:

1. A process for the preparation of a morphinan compound (III) corresponding to the formula:

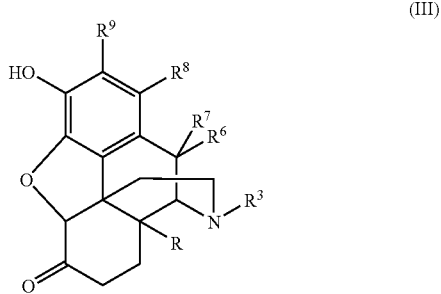

the process comprising hydrolyzing a compound (I) corresponding to the formula:

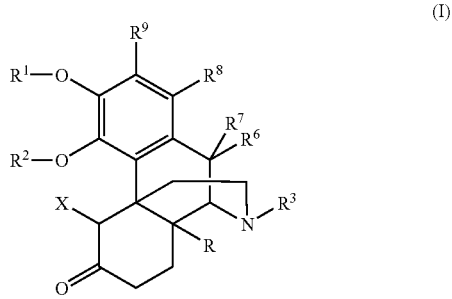

in a protic solvent to form an intermediate compound (II) corresponding to the formula:

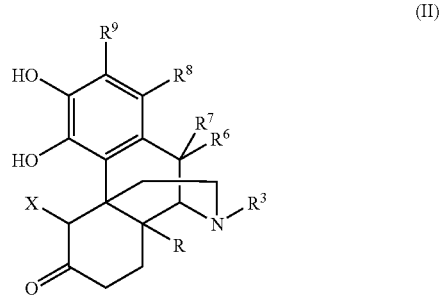

and
heating a mixture comprising an aqueous solvent and the compound (II), at a pH of about 1 to about 6, to form compound (III), wherein
R is selected from the group consisting of hydrogen, alkyl, aryl, acyl, $-SR^4$, $-OR^4$, and $-NR^4R^5$;
$R^1$ and $R^2$ are independently selected from the group consisting of hydrogen, alkyl, $B(OH)_2$, and $R^1$ and $R^2$, along with the atoms to which they are attached, form a 5-membered ring having a fifth ring member B(OH); provided, however, that at least one of $R^1$ and $R^2$ is $B(OH)_2$ or that $R^1$ and $R^2$ form the 5-membered ring;
$R^3$ is selected from the group consisting of hydrocarbyl, substituted hydrocarbyl, and a nitrogen protecting group;
$R^4$ and $R^5$ are independently selected from the group consisting of hydrogen, alkyl, aryl, and acyl;
$R^6$ and $R^7$ are independently selected from the group consisting of hydrogen, halogen, hydroxyl, $NH_2$, SH, hydrocarbyl, and substituted hydrocarbyl, wherein $R^6$ and $R^7$ may together form a group selected from the group consisting of =O and =S;
$R^8$ and $R^9$ are independently selected from the group consisting of hydrogen, halogen, hydroxyl, $NH_2$, CN, hydrocarbyl, and substituted hydrocarbyl; and
X is selected from the group consisting of chloro, bromo, and iodo.

2. The process of claim 1, wherein $R^3$ is selected from the group consisting of alkyl, allyl, aryl, and acyl.

3. The process of claim 1, wherein the protic solvent is selected from the group consisting of water, methanol, ethanol, isopropyl alcohol, and combinations thereof, the mixture is heated to a temperature of about 60° C. to about 90° C.; the mixture is adjusted to a pH of about 2 to about 4; X is bromo; $R^3$ is alkyl; R is selected from the group consisting of hydrogen and hydroxyl; $R^7$ is methyl; and $R^8$ is hydroxyl.

4. The process of claim 1, wherein one of $R^1$ and $R^2$ is hydrogen and the other of $R^1$ and $R^2$ is $B(OH)_2$ or $R^1$ and $R^2$, together with the atoms to which they are attached, form the 5-membered ring.

5. The process of claim 1, wherein the optical activity of compounds (I), (II), and (III) is (−) or (+), and the configuration of C13, C14, and C9, respectively, of compounds (I) and (II) is selected from the group consisting of RRR, RRS, RSR, RSS, SRR, SRS, SSR, and SSS, and the configuration of C5, C13, C14, and C9, respectively, of compound (III) is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS.

6. A process for the preparation of a morphinan compound (III) corresponding to the formula:

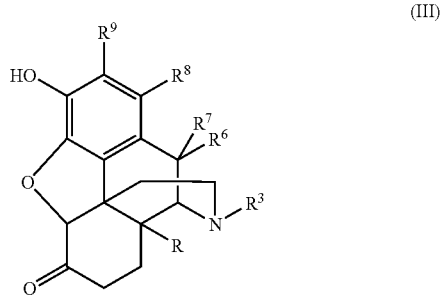

the process comprising heating a mixture comprising an aqueous solvent and a compound (II) corresponding to the formula:

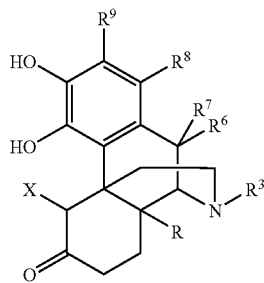

(II)

at a pH of about 1 to about 6 to form compound (III), wherein:
R is selected from the group consisting of hydrogen, alkyl, aryl, acyl, —SR$^4$, —OR$^4$, and —NR$^4$R$^5$;
R$^3$ is selected from the group consisting of hydrocarbyl, substituted hydrocarbyl, and a nitrogen protecting group;
R$^4$ and R$^5$ are independently selected from the group consisting of hydrogen, alkyl, aryl, and acyl;
R$^6$ and R7 are independently selected from the group consisting of hydrogen, halogen, hydroxyl, NH$_2$, SH, hydrocarbyl, and substituted hydrocarbyl, wherein R$^6$ and R$^7$ may together form a group selected from the group consisting of =O and =S;
R$^8$ and R$^9$ are independently selected from the group consisting of hydrogen, halogen, hydroxyl, NH$_2$, CN, hydrocarbyl, and substituted hydrocarbyl; and
X is selected from the group consisting of chloro, bromo, and iodo.

7. The process of claim 6, wherein R$^3$ is selected from the group consisting of alkyl, allyl, aryl, and acyl.

8. The process of claim 6, wherein the mixture is heated to a temperature of about 60° C. to about 90° C.; the mixture is adjusted to a pH of about 2 to about 4; X is bromo; R$^3$ is alkyl; and R is selected from the group consisting of hydrogen and hydroxyl.

9. The process of claim 6, wherein the optical activity of compounds (I), (II), and (III) is (−) or (+), and the configuration of C13, C14, and C9, respectively, of compounds (I) and (II) is selected from the group consisting of RRR, RRS, RSR, RSS, SRR, SRS, SSR, and SSS, and the configuration of C5, C13, C14, and C9, respectively, of compound (III) is selected from the group consisting of RRRR, RRSR, RRRS, RRSS, RSRR, RSSR, RSRS, RSSS, SRRR, SRSR, SRRS, SRSS, SSRR, SSSR, SSRS, and SSSS.

10. A morphinan compound, or pharmaceutically acceptable salt thereof, the compound corresponding to the formula:

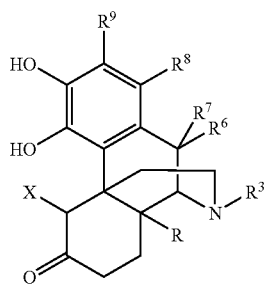

(II)

wherein:
R is selected from the group consisting of hydrogen, alkyl, aryl, acyl, —SR$^4$, —OR$^4$, and —NR$^4$R$^5$;
R$^3$ is selected from the group consisting of alkyl, aryl, acyl, and a nitrogen protecting group;
R$^4$ and R$^5$ are independently selected from the group consisting of hydrogen, alkyl, aryl, and acyl;
R$^6$ and R$^7$ are independently selected from the group consisting of hydrogen, halogen, hydroxyl, NH$_2$, SH, hydrocarbyl, and substituted hydrocarbyl, wherein R$^6$ and R$^7$ may together form a group selected from the group consisting of =O and =S;
R$^8$ and R$^9$ are independently selected from the group consisting of hydrogen, halogen, hydroxyl, NH$_2$, CN, hydrocarbyl, and substituted hydrocarbyl; and
X is selected from the group consisting of chloro, bromo, and iodo.

11. The compound of claim 10, wherein X is bromo; R$^3$ is alkyl; and R is selected from the group consisting of hydrogen and hydroxyl.

12. The compound of claim 11, wherein R$^3$ is selected from the group consisting of methyl, cyclopropyl, isobutyl, and cyclobutyl.

13. The compound of claim 10 comprising the structure:

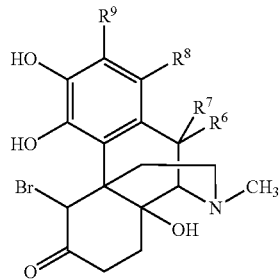

wherein:
R$^6$ and R$^7$ are independently selected from the group consisting of hydrogen, halogen, hydroxyl, NH$_2$, SH, hydrocarbyl, and substituted hydrocarbyl, wherein R$^6$ and R$^7$ may together form a group selected from the group consisting of =O and =S; and
R$^8$ and R$^9$ are independently selected from the group consisting of hydrogen, halogen, hydroxyl, NH$_2$, CN, hydrocarbyl, and substituted hydrocarbyl.

14. The compound of claim 10, wherein the optical activity of the compound is (−) or (+), and the configuration of C13, C14, and C9, respectively, is selected from the group consisting of RRR, RRS, RSR, RSS, SRR, SRS, SSR, and SSS.

15. A morphinan compound, or pharmaceutically acceptable salt thereof, the compound corresponding to the formula:

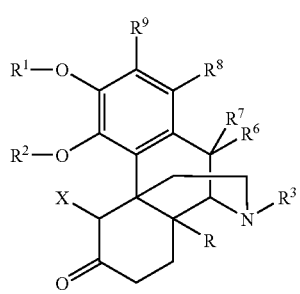

(I)

wherein:
- R is selected from the group consisting of hydrogen, alkyl, aryl, acyl, —$SR^4$, —$OR^4$, and —$NR^4R^5$;
- $R^1$ and $R^2$ are independently selected from the group consisting of hydrogen, alkyl, $B(OH)_2$, and $R^1$ and $R^2$, along with the atoms to which they are attached, form a 5-membered ring having a fifth ring member B(OH); provided, however, that at least one of $R^1$ and $R^2$ is $B(OH)_2$ or that $R^1$ and $R^2$ form the 5-membered ring;
- $R^3$ is selected from the group consisting of alkyl, aryl, acyl, and a nitrogen protecting group;
- $R^4$ and $R^5$ are independently selected from the group consisting of hydrogen, alkyl, aryl, and acyl;
- $R^6$ and $R^7$ are independently selected from the group consisting of hydrogen, halogen, hydroxyl, $NH_2$, SH, hydrocarbyl, and substituted hydrocarbyl, wherein $R^6$ and $R^7$ may together form a group selected from the group consisting of =O and =S;
- $R^8$ and $R^9$ are independently selected from the group consisting of hydrogen, halogen, hydroxyl, $NH_2$, CN, hydrocarbyl, and substituted hydrocarbyl; and
- X is selected from the group consisting of chloro, bromo, and iodo.

16. The compound of claim 15, wherein X is bromo; $R^3$ is alkyl; and R is selected from the group consisting of hydrogen and hydroxyl.

17. The compound of claim 16, wherein $R^3$ is selected from the group consisting of methyl, cyclopropyl, isobutyl, and cyclobutyl.

18. The compound of claim 15 having the structure:

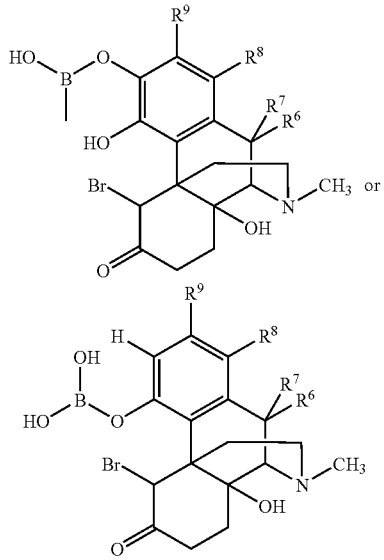

wherein:
- $R^6$ and $R^7$ are independently selected from the group consisting of hydrogen, halogen, hydroxyl, $NH_2$, SH, hydrocarbyl, and substituted hydrocarbyl, wherein $R^6$ and R7 may together form a group selected from the group consisting of =O and =S; and
- $R^8$ and $R^9$ are independently selected from the group consisting of hydrogen, halogen, hydroxyl, $NH_2$, CN, hydrocarbyl, and substituted hydrocarbyl.

wherein:
- $R^6$ and $R^7$ are independently selected from the group consisting of hydrogen, halogen, hydroxyl, $NH_2$, SH, hydrocarbyl, and substituted hydrocarbyl, wherein R6 and $R^7$ may together form a group selected from the group consisting of =O and =S; and
- $R^8$ and $R^9$ are independently selected from the group consisting of hydrogen, halogen, hydroxyl, $NH_2$, CN, hydrocarbyl, and substituted hydrocarbyl.

19. The compound of claim 15 having the structure:

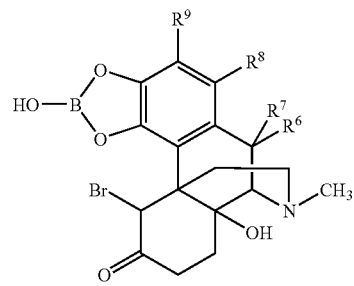

20. The compound of claim 15, wherein the optical activity of the compound is (−) or (+), and the configuration of C13, C14, and C9, respectively, is selected from the group consisting of RRR, RRS, RSR, RSS, SRR, SRS, SSR, and SSS.

* * * * *

UNITED STATES PATENT AND TRADEMARK OFFICE
CERTIFICATE OF CORRECTION

PATENT NO. : 7,999,105 B2
APPLICATION NO. : 12/372788
DATED : August 16, 2011
INVENTOR(S) : Peter X. Wang et al.

It is certified that error appears in the above-identified patent and that said Letters Patent is hereby corrected as shown below:

Column 19, lines 32-42

The first formula in Claim 18 currently reads:

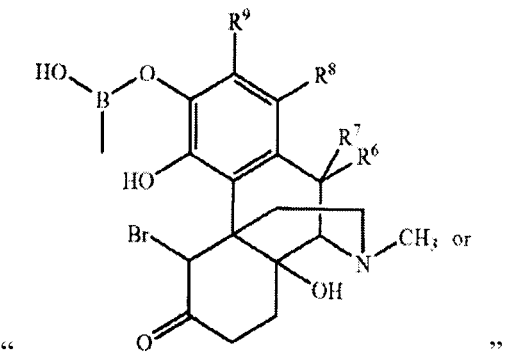

" "

First formula in Claim 18 should read:

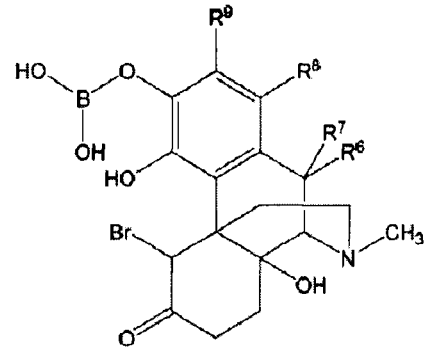

-- --

Signed and Sealed this
Twenty-third Day of July, 2013

Teresa Stanek Rea
*Acting Director of the United States Patent and Trademark Office*